United States Patent
Mosler et al.

(10) Patent No.: US 9,615,945 B2
(45) Date of Patent: Apr. 11, 2017

(54) PROSTHETIC VALVE AND VACUUM ADAPTER SYSTEM

(71) Applicant: OTTO BOCK HEALTHCARE GMBH, Duderstadt (DE)

(72) Inventors: Luder Mosler, Duderstadt (DE); Martin Hillmann, Duderstadt (DE); Andre Muller, Duderstadt (DE); Mark Schonemeier, Gottingen (DE)

(73) Assignee: OTTO BOCK HEALTHCARE GMBH, Duderstadt (DE)

( * ) Notice: Subject to any disclaimer, the term of this patent is extended or adjusted under 35 U.S.C. 154(b) by 0 days.

(21) Appl. No.: 14/360,914

(22) PCT Filed: Nov. 29, 2012

(86) PCT No.: PCT/EP2012/004931
§ 371 (c)(1),
(2) Date: May 27, 2014

(87) PCT Pub. No.: WO2013/079202
PCT Pub. Date: Jun. 6, 2013

(65) Prior Publication Data
US 2014/0296998 A1 Oct. 2, 2014

(30) Foreign Application Priority Data

Nov. 29, 2011 (DE) .......................... 10 2011 119 593
Jun. 14, 2012 (DE) .......................... 10 2012 011 681

(51) Int. Cl.
*A61F 2/74* (2006.01)
*A61F 2/80* (2006.01)

(52) U.S. Cl.
CPC .......... *A61F 2/80* (2013.01); *A61F 2002/748* (2013.01); *A61F 2002/802* (2013.01); *A61F 2002/805* (2013.01)

(58) Field of Classification Search
CPC ...... A61F 2/76; A61F 2/80; A61F 2002/5016; A61F 2002/5018; A61F 2002/5032;
(Continued)

(56) References Cited

U.S. PATENT DOCUMENTS 3,901,272 A * 8/1975 Banners ................ F16K 15/147
137/513.5
4,143,853 A * 3/1979 Abramson ............ A61M 39/26
137/515.7
(Continued)

FOREIGN PATENT DOCUMENTS

DE 746781 C 8/1944
EP 1875881 A1 1/2008
(Continued)

OTHER PUBLICATIONS

PCT International Search Report for PCT International Patent Application No. PCT/EP2012/004931, mailed Mar. 6, 2013.

*Primary Examiner* — Thomas J Sweet
*Assistant Examiner* — Christie Bahena
(74) *Attorney, Agent, or Firm* — Holland & Hart LLP

(57) ABSTRACT

A device for connecting a pump, having a through-hold provided in a prosthesis shaft, wherein the device comprises at least one channel having a first outlet for connecting to the through-hole in the prosthesis shaft and a second outlet which can be connected to the pump and at least one valve, wherein the valve can be switched to a first mode and to a second mode, and the valve is a one-way valve in the first mode and a two-way valve in the second mode.

17 Claims, 22 Drawing Sheets

(58) Field of Classification Search
CPC .......... A61F 2002/742; A61F 2002/748; A61F
2002/802; A61F 2002/805; A61F
2002/807; F16K 15/147; F16K 15/185;
A16K 7/16
USPC .................. 604/247, 905; 251/149.1; 13/144
See application file for complete search history.

(56) References Cited

U.S. PATENT DOCUMENTS

| | | | | |
|---|---|---|---|---|
| 4,341,239 | A | * | 7/1982 | Atkinson ............... F16K 15/147 137/493 |
| 5,249,598 | A | * | 10/1993 | Schmidt ........... B60K 15/03519 137/493.1 |
| 5,702,489 | A | | 12/1997 | Slemker |
| 6,063,125 | A | * | 5/2000 | Arbogast ................. A61F 2/76 623/34 |
| 6,926,742 | B2 | | 8/2005 | Caspers et al. |
| 7,025,744 | B2 | * | 4/2006 | Utterberg ............... A61M 39/02 604/256 |
| 7,427,298 | B1 | | 9/2008 | Swanson, Sr. |
| 7,927,377 | B2 | | 4/2011 | Slemker et al. |
| 2002/0117645 | A1 | * | 8/2002 | Kiehne ................ F16K 15/147 251/149.6 |
| 2004/0204771 | A1 | * | 10/2004 | Swanson, Sr. ......... A61F 2/5046 264/222 |
| 2004/0260403 | A1 | | 12/2004 | Patterson et al. |
| 2005/0143838 | A1 | * | 6/2005 | Collier ..................... A61F 2/60 623/34 |
| 2005/0240282 | A1 | * | 10/2005 | Rush ......................... A61F 2/60 623/26 |
| 2006/0282175 | A1 | * | 12/2006 | Haines ..................... A61F 2/68 623/24 |
| 2007/0213839 | A1 | * | 9/2007 | Nachbar ................... A61F 2/60 623/26 |
| 2009/0281637 | A1 | | 11/2009 | Martin |
| 2010/0087931 | A1 | * | 4/2010 | Bogue ...................... A61F 2/78 623/34 |
| 2010/0094432 | A1 | * | 4/2010 | Mackenzie ............... A61F 2/68 623/34 |
| 2010/0125342 | A1 | | 5/2010 | King |
| 2011/0184532 | A1 | | 7/2011 | Tompkins |

FOREIGN PATENT DOCUMENTS

| | | |
|---|---|---|
| WO | 8400881 A1 | 3/1984 |
| WO | 2006135851 A2 | 12/2006 |
| WO | 2010036370 A1 | 4/2010 |

* cited by examiner

PROSTHETIC VALVE AND VACUUM ADAPTER SYSTEM

TECHNICAL FIELD

The invention relates to a device for connecting a pump to a through-bore which is provided in a prosthesis shaft, wherein the device includes at least one channel with a first orifice for connecting to the outlet opening provided in the prosthesis shaft and a second orifice which is connectable to the pump, and includes at least one valve.

BACKGROUND

A device of this type is known, for example, from U.S. Pat. No. 5,702,489 A.

In order to fasten a prosthesis system securely to an amputation stump of a patient, negative pressure is frequently generated between the amputation stump or a liner pulled over the same, for example produced from an elastomer, and the prosthesis shaft. Between the prosthesis shaft and the liner, which is pulled over an amputation stump, there is generated an inner volume which it is necessary to evacuate. As a rule, the prosthesis shaft has a distal through-bore for this purpose to which a vacuum pump is connected. An arrangement of this type is known, for example, from WO 2006/135851 A2. In this case, the vacuum pump together with a power supply provided for it is part of the prosthesis structure. A switch by means of which the vacuum pump can be activated is arranged on the prosthesis structure itself such that the wearer of the prosthesis system is himself able to set the negative pressure which is acceptable to him and is necessary so that the prosthesis system sits in a fixed manner.

If a prosthesis system of this type is worn over a longer period, for example a day, it is possible for air to penetrate into the inner volume between the liner and the prosthesis shaft as a result of the movement of the amputation stump and of the prosthesis system as well as a result of small leakages. This causes the negative pressure to decrease, as a result of which the fastening of the prosthesis system to the amputation stump is weakened.

The advantage of the embodiment provided in WO 2006/135851 A2 is that the wearer of the prosthesis system always carries the vacuum pump on him as it is part of the prosthesis system. If, as a result of penetrated air, the adhesive effect of the prosthesis system were to be reduced, the wearer can simply activate the vacuum pump by means of the switch and thus re-establish the optimum pressure. If the pressure is measured by means of a sensor, the pump can also be automatically activated. However, a disadvantage of the embodiment shown is that, on the one hand, a sufficient power supply, for example provided by batteries, always has to be provided for the vacuum pump and, on the other hand, both the weight of said power supply and that of the vacuum pump have to be taken along. In addition, it is possible, in particular in the case of short prosthesis systems, for there not to be enough space on the prosthesis system itself to accommodate the vacuum pump and its power supply in the most unobtrusive manner possible.

Consequently, the provision of an external vacuum pump is known, for example from U.S. Pat. No. 5,702,489 and U.S. Pat. No. 6,926,742.

In U.S. Pat. No. 5,702,489 an adapter element is arranged between the prosthesis shaft and the remaining prosthesis structure for this purpose. Said adapter element has a channel, the one orifice of which is connected to the through-bore which is provided in the prosthesis shaft. A connecting device to which, for example, the pump is connected, is provided at the other end of the channel which exits laterally out of the adapter element. A needle valve, by means of which the channel can be closed when no pump is connected to the second output, is provided in between.

A disadvantage of said system is that the wearer of the prosthesis system can only equalize a possible loss of pressure between the liner and the prosthesis shaft if he brings along with him a vacuum pump as a separate tool. In addition, he then has to connect said vacuum pump to the corresponding device of the prosthesis system or of the adapter element, which is difficult to impossible in particular for older or mobility-challenged wearers of prosthesis systems. In addition, the valve which closes the second orifice of the channel when no pump is connected can be opened even without a connected vacuum pump. In this case, air penetrates through the channel into the inner volume such that the prosthesis no longer adheres to the amputation stump.

At least to remedy said last disadvantage, WO 2010/036370 A1 proposes providing at one end of the channel a non-return valve which reliably prevents ingress of air into the inner volume. If a negative pressure pump is connected to the second orifice of the channel, air can nevertheless be pumped out of the inner volume as the non-return valve enables through-flow in said direction. The advantage of said arrangement where air is not able to ingress into the inner volume is at the same time its disadvantage. In particular when the wearer of the prosthesis system wants to put the prosthesis down, it is advantageous to refill the inner volume with air. This is not possible in the case of the embodiment shown there as the non-return valve prevents this in a secure manner. In addition, the disadvantage of a fixed non-return valve is that the opening pressure of the valve falsifies the measuring of the negative pressure. With a return flow through the pump, the control system registers a drop in negative pressure which is, however, not present in the shaft.

SUMMARY

Consequently, it is the object of the invention to provide a device and a prosthesis system which eliminates the aforementioned disadvantages from the prior art.

The invention achieves the object set by a generic device where the valve is movable into a first mode and into a second mode, wherein the valve is a one-way valve in the first mode and a two-way valve in the second mode. A device of this type can be incorporated, in this case, into part of a prosthesis system, for instance the prosthesis shaft or can be realized as a separate component. This is then arranged as an adapter element for example between the prosthesis shaft and a prosthesis structure. The first orifice of the at least one channel, in this case, can be connected either directly to part of the prosthesis shaft or by means of connecting element, for example a hose, to the through-bore in the prosthesis shaft.

If a device according to the invention is then used, for instance by being arranged between a prosthesis shaft and a prosthesis structure, a pump can be mounted on said device. In this case, the pump is connected to the second orifice of the at least one channel of the device. It is particularly advantageous when, as a result of arrangement of the pump, the valve is already moved into the second mode. In the second mode, the valve is a two-way valve such that air is able to flow in both directions through the channel. If then a prosthesis system in which a device of this type is used is put on by the wearer, a negative pressure pump can be arranged at the second channel orifice of the device, as a result of which the inner volume between prosthesis shaft and the liner or the amputation stump is able to be evacuated. If, in contrast, a prosthesis system of this type is taken off by the wearer, an overpressure pump can be connected to the second channel orifice of the device. If the valve, in this case, is in the second mode, being therefore a two-way valve, air can also be pumped into the inner volume between the prosthesis shaft and the liner or the amputation stump such that the prosthesis shaft and consequently the prosthesis system can be easily released from the amputation stump. If, however, no pump is arranged at the second channel orifice of the device, the valve is situated in an advantageous manner in the first mode. In this case the valve is a one-way valve which, in a particularly preferred development, only enables flow in the direction from the first orifice to the second orifice of the channel. In this case, it is therefore only possible for air to be pressed out of the inner volume without air being able to pass in from the outside.

Should then air ingress into the inner volume as a result of movements of the wearer of the prosthesis system or as a result of small leakages, said air is pressed out of the inner volume the next time the prosthesis is loaded. In this case, it flows through the channel from the first orifice in the direction of the second orifice, which is also possible in the first mode of the valve when it is therefore a one-way valve. Consequently all the disadvantages from the prior art are eliminated in a particularly simple and secure manner. A loss of pressure that occurs over the course of the day and a resultant decreasing adhesive effect are reliably prevented by said development. In addition, as a result of the particular development of the valve it is possible for the wearer both to put on and to take off the prosthesis system in a simple and quick manner.

It has proved advantageous when the valve includes a diaphragm. The valve can be realized, for example, as a spout or dome valve and with single or double slots. In this case, the valve is then movable from the first mode into the second mode by the diaphragm being pushed through for example by a push-through element which, in a particularly preferred embodiment, includes a passage, or is opened by pressure applied onto the diaphragm. If the push-through element is removed again, the diaphragm is closed and the valve is operated in the first mode as a one-way valve again.

In an advantageous manner, the at least one channel additionally comprises a third orifice for connecting to the through-bore provided in the prosthesis shaft and a closure element which is connectable to the third orifice and in a connected state prevents inflow through the third orifice into the at least one channel. The device is usable in a flexible manner in this way. Thus, the first orifice can be provided, for example, on a side of the device that faces the prosthesis shaft, and can thus be connectable directly to part of the prosthesis shaft. The third orifice of the at least one channel, in this case, can be arranged on a different side of the device. Consequently, a connecting element, for example a hose, by way of which the third orifice of the at least one channel can be connected to the through-bore in the prosthesis shaft, can be arranged at said position. This is advantageous in particular for the case where the through-bore provided in the prosthesis shaft is not arranged at a position which is facing the device in the connected state. In this way the device can be used in a flexible manner for the most varied developments of prosthesis shafts.

The closure element, which is connectable to the third orifice and in this state prevents inflow, ensures that even for the case where the first orifice is connected to the through-bore in the prosthesis shaft, it is possible to generate a vacuum inside the prosthesis shaft between the prosthesis shaft and the amputation stump of the patient without additional air flowing in through the third orifice of the at least one channel.

It has been proven as particularly advantageous when the closure element comprises a one-way valve which, with the closure element connected to the third orifice, only allows outflow through the third orifice out of the at least one channel. When a prosthesis is put on with a prosthesis shaft where the pump is connected by means of a device of this type to the through-bore in the prosthesis shaft for generating the vacuum, air present in the prosthesis shaft can consequently initially leave the prosthesis shaft through the one-way valve. Consequently, the pump does not have to be used for this purpose such that on the one hand energy is saved and consequently the running time of the pump can be lengthened and in addition an unpleasant, perturbing noise load produced by a starting pump can be prevented. In addition, smaller leakages which lead to inflow of air into the region between the prosthesis shaft and the amputation stump can be compensated as a result of said air leaving the prosthesis system through the one-way valve in the closure element just as a result of, for example, a walking movement of the patient, without the pump having to be started up, used or removed for this purpose.

A device according to one exemplary embodiment of the present invention simply needs to be realized such that it is able to connect a through-bore provided in a prosthesis shaft to a pump. If it is realized as an adapter element, the device can consequently also be used in conventional prosthesis systems according to the prior art which can consequently be retrofitted in a simple manner. In a preferred manner, in this case, a system is provided with an adapter element of the afore-described type as well as a pump with a pump housing, wherein connecting means, which correspond with one another and by way of which the adapter element is connectable to the pump housing, are realized on the pump housing and on the device.

In this way it is ensured in a particularly simple manner that, on the one hand, a suitable pump is always provided for the respective adapter element, and that, on the other hand, the two components are connected together in a secure and simple manner. To this end, in a particularly preferred manner said connecting means can be realized, for example, as at least one groove and at least one tongue which corresponds to the groove. In this case, the groove or the tongue is arranged on the adapter element and the respective other connecting means is arranged on the pump housing. In this way, the adapter element and the pump housing can be simply fitted into one another such that a secure connection is provided here. Naturally, said type of fastening of the pump on the device is also advantageous when the device is not realized as a separate adapter element, but is incorporated into another component of the prosthesis system.

In a preferred manner, the connecting means include a connecting plate which is provided on the device. Said connecting plate is, for example, provided with elements into which the pump housing can latch or snap. As an alternative to this or in addition to it, it is also possible to provide a separate fastening element which, where required, can be fastened on the connecting plate. The pump is then fastenable on said fastening element. The advantage of said development is that possible projections which are arranged on the connecting plate and can be necessary for the arrangement of the pump directly on the connecting plate, no longer have to be present and can consequently no longer be broken off inadvertently or damaged in any other manner by the wearer of the prosthesis system.

The pump can also be connected non-detachably to the connecting plate, for example can be laminated thereon. The connecting plate can be fastened on the device for example by means of a snap-type element or a latch-type element or even by means of a screw-type connection.

An outwardly projecting pin, which is realized in such a manner that it pushes through the diaphragm when the pump housing is connected to the device, is preferably arranged on the pump housing. If, therefore, the pump housing is then connected to the device, the pin penetrates into the second orifice of the channel of the device. In this case, it pushes through the diaphragm which comprises the valve that is arranged behind the second orifice. The valve is moved from the first mode into the second mode in this way such that the pump is then able both to suck air through the at least one channel of the device and to pump air through it. As an alternative to this, the pin is developed such that it presses onto the outside faces of the diaphragm realized as a spout or dome and thus opens the diaphragm. In this case, the pressure is applied in a preferred manner in edge regions of the diaphragm such that an opening is produced in the central region in which a slot is provided.

In order to ensure a secure connection between the pump housing and the device, a force-applying element is preferably arranged both on the pump housing and on the device, said force-applying elements together producing a force when the pump housing is connected to the device. Said force, in this case, counters the releasing of the pump housing from the device. Magnetic elements which have opposite poles and consequently mutually attract can be provided, for example, as a particularly simple development of such types of force-applying elements. Inadvertent release of the pump housing from the device during the pumping operation is consequently made at least more difficult. As an alternative to this or in addition to it, it is possible to provide latch-type and/or snap-type elements, as a result of which inadvertent release of the pump housing is made even more difficult.

In a preferred development in each case at least one insert bore is arranged both on the pump housing and on the device, said insert bores being aligned with one another in the connected state such that a plug-in element is guidable through the insert bores. In this way, a further connection, which can be realized in particular in a positive locking manner, is achieved between the device and the pump housing, by means of which, on the one hand, the device and the pump housing are arranged in optimum positioning in relation to one another, and which, on the other hand, is also easy for the user of a corresponding prosthesis system to release. In a preferred manner, the plug-in element is realized, for example, in the form of a socket wrench which can be used to remove or tighten screws from or on the prosthesis system. In this way, it is possible, for example, in a particularly simple manner to secure, for instance, the cover of a battery compartment with screws such that inadvertent opening is avoided, and at the same time to ensure that the tool required to open the battery compartment is carried on the prosthesis system and at the same time fulfils a stabilizing and securing function.

A prosthesis system according to the invention preferably includes a prosthesis shaft, a device and a prosthesis structure. In a particularly advantageous manner, it also includes a pump with an above-described pump housing.

As a result of a device according to the exemplary embodiments of the present invention, it is consequently possible to connect an active negative pressure pump and an overpressure pump to the prosthesis system and thus to enable the sucking up of air out of the inner volume or the pumping in of air into the inner volume. The valve on the device, in this case, functions in the first mode as a passive expelling valve through which air located in an unwanted manner in the inner volume is able to be expelled, whilst in the second mode it serves as access to the inner volume for the respectively arranged pump. As a result of the advantageous development of the pump housing such that it is directly connectable to the device, it is no longer necessary, unlike the prior art, to provide a separate hose which connects the prosthesis system or the device to a separate pump. As a result, both expenditure on hardware is reduced and connection of the pump to the prosthesis system or to the device is simplified.

The valve can also be movable from the first mode into the second mode and vice versa as a result of a switch, which is, for example, to be manually activated, or by means of another arrangement.

BRIEF DESCRIPTION OF THE DRAWINGS

An exemplary embodiment of the present invention is explained below by way of a drawing, in which, in detail.

DETAILED DESCRIPTION

Figure 1:
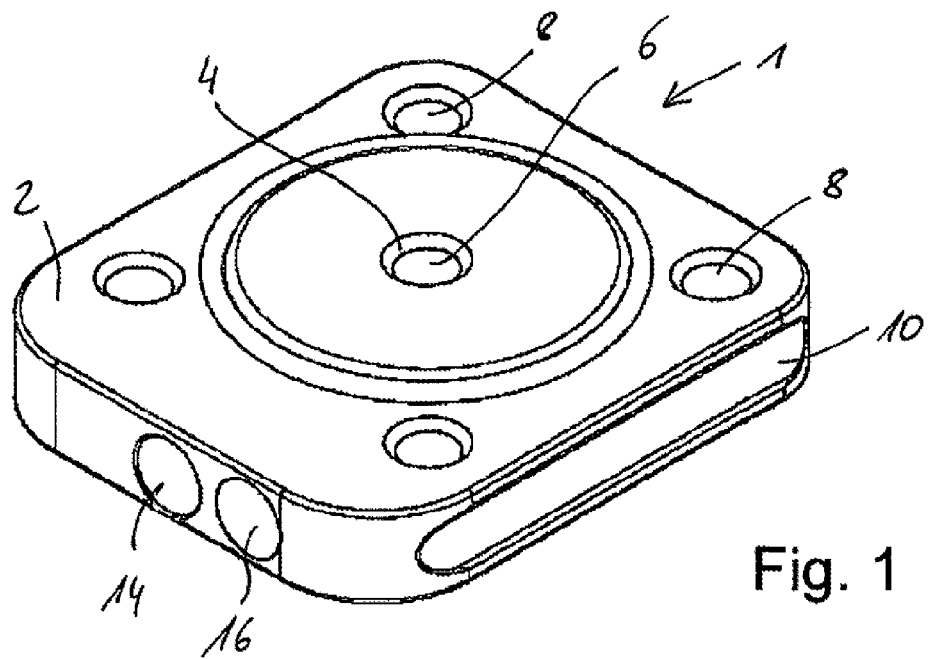
FIG. 1 shows a schematic view of a device according to a first exemplary embodiment of the present invention.

FIG. 1 shows the schematic view of a device according to a first exemplary embodiment of the present invention, the device being realized in the form of an adapter element 1. Even if the device is always shown below as an adapter element 1, the statements are also applicable to other developments of a device according to an exemplary embodiment of the present invention.

The adapter element 1 comprises a top side 2 on which it is possible to arrange a prosthesis shaft which is not shown in FIG. 1. In FIG. 1 the top side 2 comprises a first orifice 4 of an at least one channel 6. Said first orifice 4 can be connected to an outlet opening provided on the prosthesis shaft (not shown). Several bores 8, through which the connecting elements are guidable, by way of which the adapter element 1 is fastenable on the prosthesis shaft, can be seen in FIG. 1. The adapter element 1 has a groove 10 on a side face. An identical groove 10 is situated on the side face which is opposite said side face and cannot be seen in the representation shown in FIG. 1. Said two grooves are part of the connecting means 12 by means of which the adapter element 1 is connectable to a pump housing 18, which is not shown in FIG. 1.

A second orifice 14 of the channel 6 can also be seen in FIG. 1. A pump, which is not shown in FIG. 1 and by means of which the air can be pumped out of an inner volume which is formed between a prosthesis shaft and a liner or an amputation stump, is connectable to the second orifice 14. As the valve, which is situated in the interior of the adapter element 1, is operated in this case in the second mode, air can also be pumped into said inner volume.

A first force-applying element 16, which can be realized, for example, in the form of a magnet, is shown next to the second orifice 14.

Figure 2:
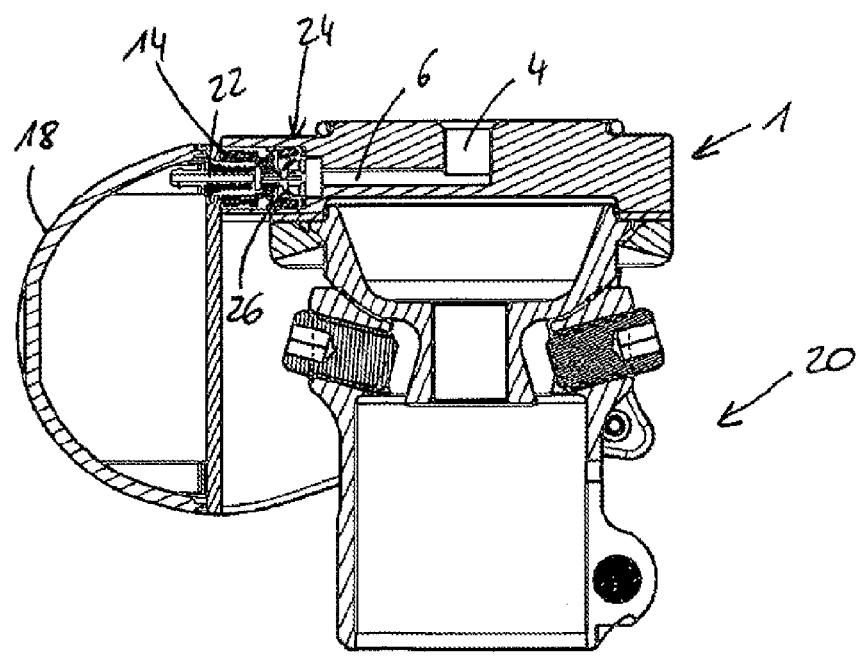
FIG. 2 shows a schematic section through part of a prosthesis system according to an exemplary embodiment of the present invention.

FIG. 2 shows a schematic representation of a section through part of a prosthesis system. The adapter element 1 with the channel 6, the first orifice 4 and the second orifice 14 can be seen. A pump with a pump housing 18 is arranged at the second orifice 14. A prosthesis structure 20, more details of which are not to be given at this point, is situated below the adapter element 1 in FIG. 2.

A pin 22, which penetrates into the orifice 14 of the channel 6 when the adapter element 1 is connected to the pump housing 18, is provided on the pump housing 18. A valve 24, which has a diaphragm 26 which is pushed through by the pin 22, is situated inside the channel. This will be explained in more detail with reference to FIG. 6.

Figure 3:
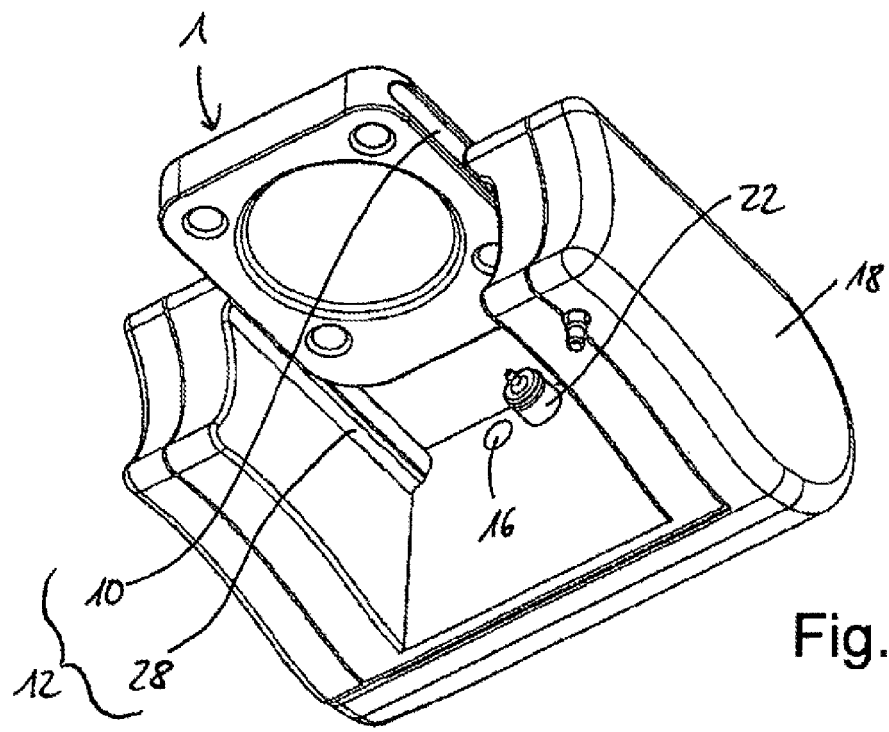
FIG. 3 shows an adapter element according to a further exemplary embodiment of the present invention when inserted into a pump housing.
Figure 4:
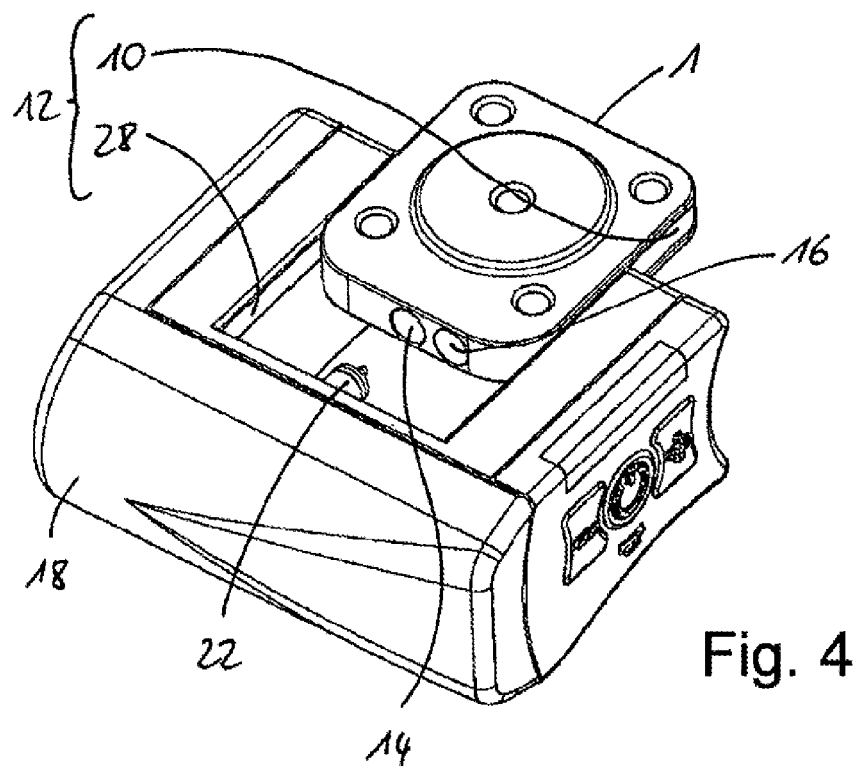
FIG. 4 shows the representation from FIG. 3 from another angle of view.

FIGS. 3 and 4 show how an adapter element 1 is connected to the pump housing 18. In this case, FIG. 3 shows a schematic view from inclinedly below whilst FIG. 4 shows a schematic view from inclinedly above. Tongue elements 28, which engage in the grooves 10 which are provided for this purpose on the adapter element 1, are provided on the pump housing 18. Grooves 10 and tongue elements 28 together form the connecting means 12. A particularly simple connection between the adapter element 1 and the pump housing 18 is possible in this manner and in addition inadvertent removal of the pump housing 18 during the pump operation is clearly made more difficult.

The pin 22 is situated in a side wall of the pump housing 18. As can be seen clearly in FIG. 4, said pin 22 penetrates into the second orifice 14 of the channel 6 where it pushes through a diaphragm 26 of the valve 24 which is not shown in FIGS. 3 and 4 and thus moves the valve from the first into the second mode. As an alternative to this, the pin 22 can also provide an opening of the diaphragm in another manner.

A force-applying element 16 is provided in each case on both the adapter element 1 and on the pump housing 18, both being realized in this case as magnetic elements. If the adapter element 1 is then connected to the pump housing 18, the two force-applying elements 16 are arranged close to one another or are even in contact with one another. As the two force-applying elements 16 are differently poled magnetic elements, they both attract such that they apply a force which counters the adapter element 1 being released from the pump housing 18. Inadvertent removal, for example during the pump operation, is made even more difficult in this manner.

Figure 5:
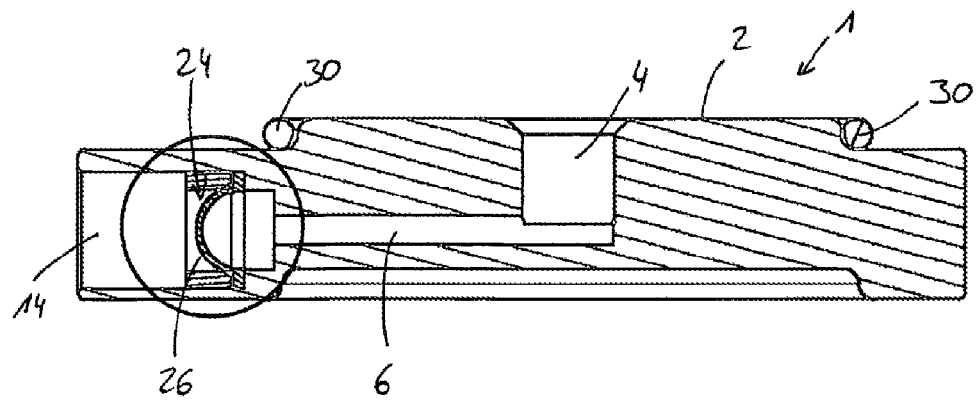
FIG. 5 shows the schematic section through an adapter element according to an exemplary embodiment of the present invention with the valve in the first mode.

FIG. 5 shows a schematic sectional representation through an adapter element 1 whilst the valve 24, which is shown encircled in FIG. 5, is in the first mode. The adapter element 1 has the channel 6 which comprises the first orifice 4 which is directed upward in FIG. 5 and the orifice 14 which is directed to the left in FIG. 5. A sealing ring 30, by means of which a connection between the adapter element 1 and the prosthesis shaft which is to be arranged at said position is to be secured, is arranged on the top side 2 of the adapter element 1.

The valve 24 has the diaphragm 26 which is realized in a dome-shaped manner in the exemplary embodiment shown in FIG. 5. The valve 24 is a one-way valve in said mode. Flow through the valve 24 is only possible in one direction from the first orifice 4 to the second orifice 14 of the channel 6. The diaphragm 26 has, for example, a slot which enables such a flow.

Said development has several advantages. On the one hand, it is not possible to open the valve 24 inadvertently in such a manner that air flows through the channel 6 in the direction of the first orifice 4. If the adapter element 1 is arranged on a prosthesis shaft in said state in which the valve 24 is in the first mode, it is thus ensured that the inner volume that is situated between the prosthesis shaft and the liner or the amputation stump cannot be filled with air. If, nevertheless, as a result of movements or leakages air does penetrate into said inner volume, the inner volume is compressed when the prosthesis is loaded. The air contained therein can penetrate into the channel 6 through the first orifice 4 and can leave the adapter element 1 again through the valve 24 which acts as a one-way valve. This ensures that the negative pressure necessary for fastening the prosthesis system to the amputation stump in a sturdy manner is maintained.

Figure 6:
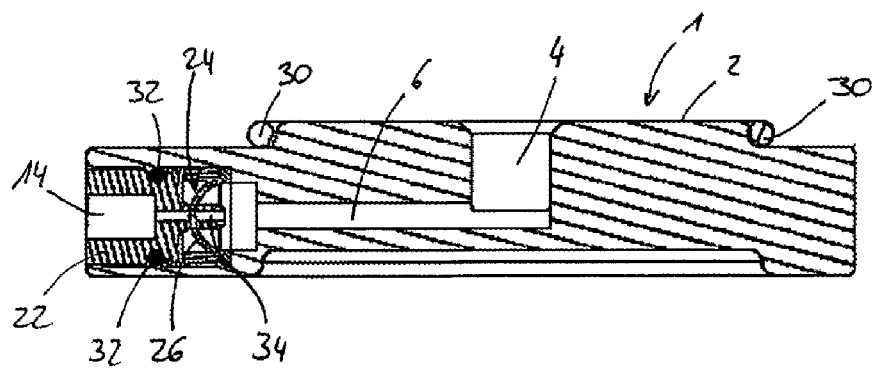
FIG. 6 shows the representation from FIG. 5 with the valve in the second mode.

FIG. 6 shows the same situation where, however, the valve 24 is in the second mode. It can be seen again that the valve 24 has a diaphragm 26. Said diaphragm is now, however, pushed through by the pin 22 which has penetrated in the second orifice 14 and which, as shown in FIGS. 2 to 4, can be part of the pump housing 18. A further sealing ring 32 which ensures a tight connection between the pin 22 and the adapter element 1 is situated between the pin 22 and the adapter element 1.

The valve 24 is in the second mode in said state. As can clearly be seen, the pin 22 has a passage 34, through which the air from the pump housing, which is situated to the left of the pin 22 in FIG. 6, is able to penetrate into the channel 6.

Consequently, it is possible, on the one hand, to pump air out of the channel 6 of the adapter element 1 by means of a negative pressure pump which is connected to the second orifice 14. This is sensible in particular when an inner volume, which is situated between a prosthesis shaft situated on the adapter element 1 and the liner, is to be evacuated. On the other hand, it is also possible in said module of the valve 24 to pump air into the channel 4 by means of a connected overpressure pump. This is sensible in particular when the prosthesis system is to be taken off by the wearer. In this way, the inner volume between the prosthesis shaft (not shown) and the amputation stump is filled with air such that the adhesive effect produced by the negative pressure is lifted. The diaphragm 26 of the valve 24 can consist, for example, of an elastomer, such as a fluoro-elastomer or silicone. In an advantageous manner the valve 24 is a slot valve or a cross slot valve or a dome valve. The important point is simply that the diaphragm 26 is able to be pushed through by the pin 22 or can be opened by pressure so that the valve 24 is operated in the second mode, and that the diaphragm 26 closes again and is ready to function when the pin 22 is removed out of the diaphragm 26. In this way it is possible to use the valve 24 in the adapter element 1 as a one-way valve in the first mode and as a two-way valve in the second mode. By the pin 22 being part of the pump housing 18, when the pump is removed from the adapter element 1 the pin 22 is also pulled out of the diaphragm 26 of the valve 24. Consequently, the valve 24 is moved from the second mode into the first mode again such that negative pressure, which is produced, for example, by a connected negative pressure pump, is maintained in the inner volume between the prosthesis shaft and the liner.

Figure 7:
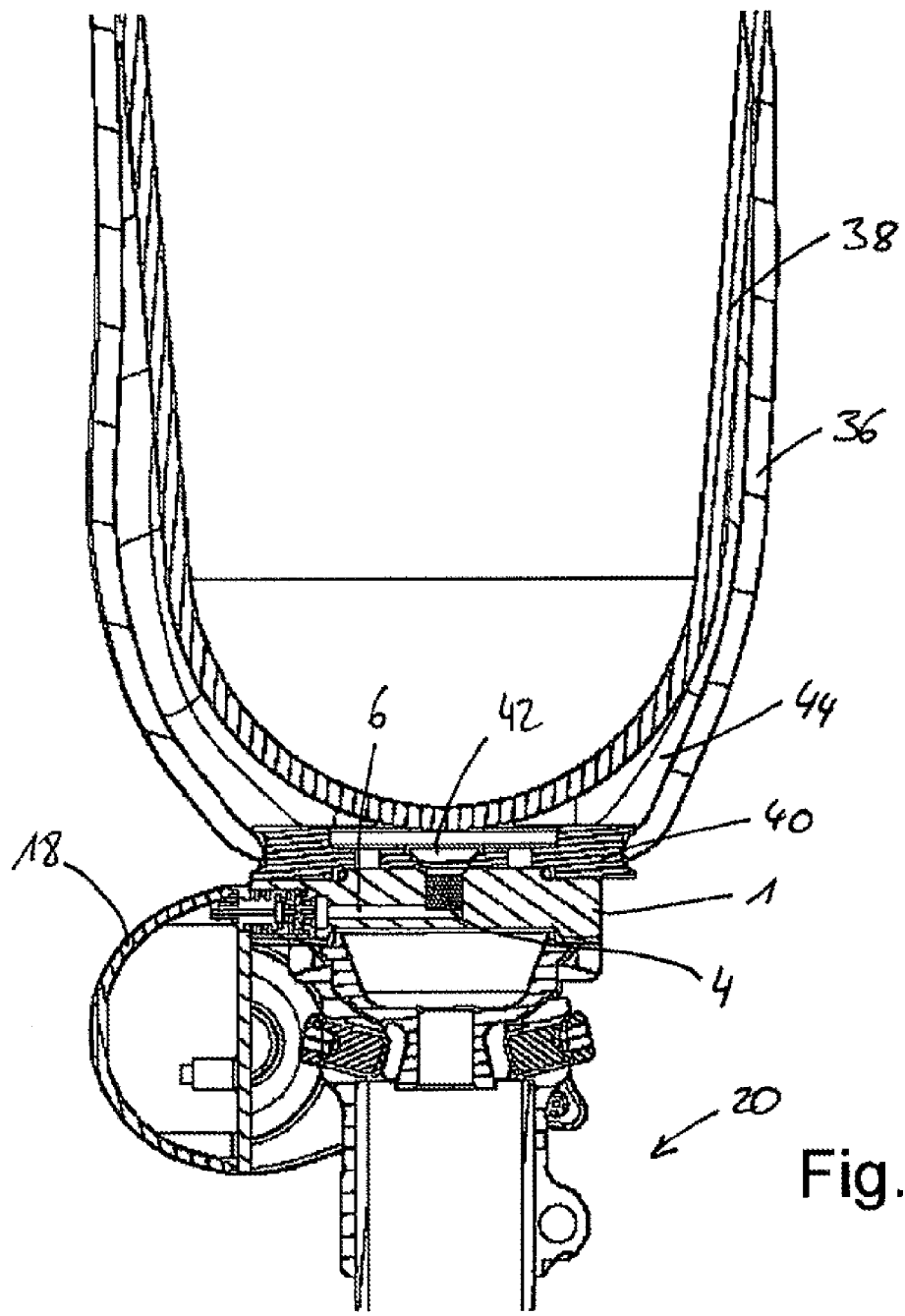
FIG. 7 shows a schematic section through part of a prosthesis system according to a further exemplary embodiment of the present invention.

FIG. 7 shows a detail from the prosthesis system according to an exemplary embodiment of the present invention. A prosthesis stump of the patient is inserted into a prosthesis shaft 36 in which a liner 38 is situated. The adapter element 1 with the channel 6 situated therein is situated below the prosthesis shaft 36. The adapter element 1 is arranged on the prosthesis shaft 36 by means of a fastening device 40. A through-bore 42, by means of which the channel 6 of the adapter element 1 is connected to an inner volume 44 which extends between the liner 38 and the prosthesis shaft 36, is situated in the fastening device 40.

The pump housing 18 is arranged on the adapter element 1, the first orifice 4 of which is connected to the through-bore 42 of the fastening device 40, as has already been shown in FIG. 2. The prosthesis structure 20, more details of which are not to be explained here, extends downward in FIG. 7.

Figure 8:
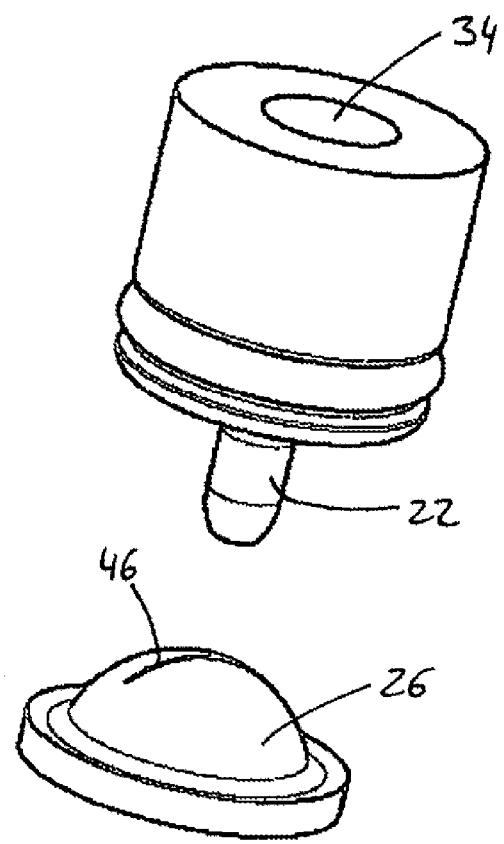
FIG. 8 shows the schematic representation of a dome valve with a first pin form.

FIG. 8 shows a schematic representation of a particular development of a dome valve. The dome-shaped diaphragm 26, which has a longitudinal slot 46 in the exemplary embodiment shown in FIG. 8, can be seen in the bottom part. The pin 22 in which the passage 34 is situated is situated above the diaphragm 26 in FIG. 8. In the situation shown in FIG. 8, flow through the diaphragm 26 is only possible in one direction from down to up. In this case, the longitudinal slot 46 in the diaphragm 26 is opened and allows the flowing medium, in the present case therefor air, to pass. Flow through the diaphragm 26 is not possible in the reverse direction as in this case the longitudinal slot 46 and consequently the diaphragm 26 remain closed. If the valve 24 is operated in said mode, there is a pressure difference in such a manner that clearly higher pressure prevails upstream of the valve 24, that is on the side of the pin 22, than downstream of the valve 24 as the valve 24 is connected on said side to the interior 44 in which negative pressure prevails. As a result of said pressure difference, the individual sides of the diaphragm 26, which are separated from one another by the longitudinal slot 46, are pulled together and closed such that no air is able to pass through the diaphragm 26 in said direction.

If the pin 22 in the exemplary embodiment shown in FIG. 8 is then moved downward, it pushes through the diaphragm 26 and penetrates through the longitudinal slot 46. As a result, the diaphragm 26 is opened such that air is also able to be directed through the passage 34 in a direction of flow from up to down.

Once the pin 22 has been pulled out of the longitudinal slot 46 of the diaphragm 26 again, the longitudinal slot 46 re-closes and flow through the diaphragm 26 is again only possible in one direction.

Figure 9:
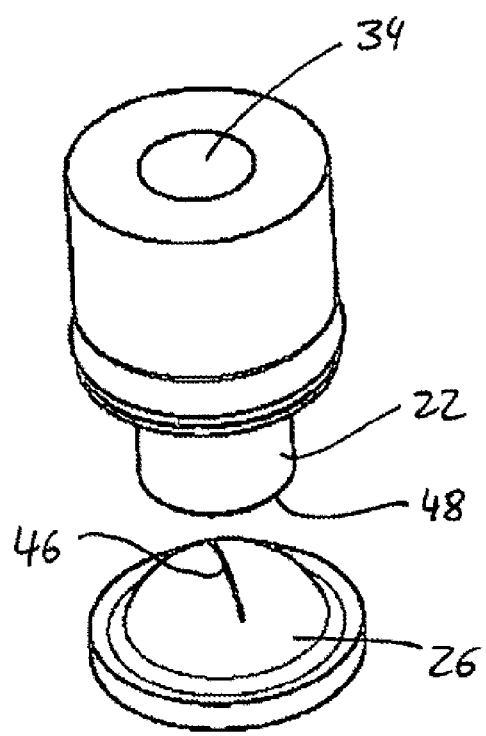
FIG. 9 shows the schematic representation of a dome valve with a second pin form.

FIG. 9 shows another development of the components shown in FIG. 8. The diaphragm 26 once again has a longitudinal slot 46. The pin 22, through which the passage 34 extends again, however, does not push through the diaphragm 26, but is provided with a pressure edge 48. If the pin 22 is then moved toward the diaphragm 26, the pin 22 does not push through the diaphragm 26 but exerts pressure onto the diaphragm 26 by means of the pressure edge 48, as a result of which the longitudinal slot 46 is also opened and the valve 24, which includes the two structural elements, is able to be used in the form of a two-way valve.

Figure 10:
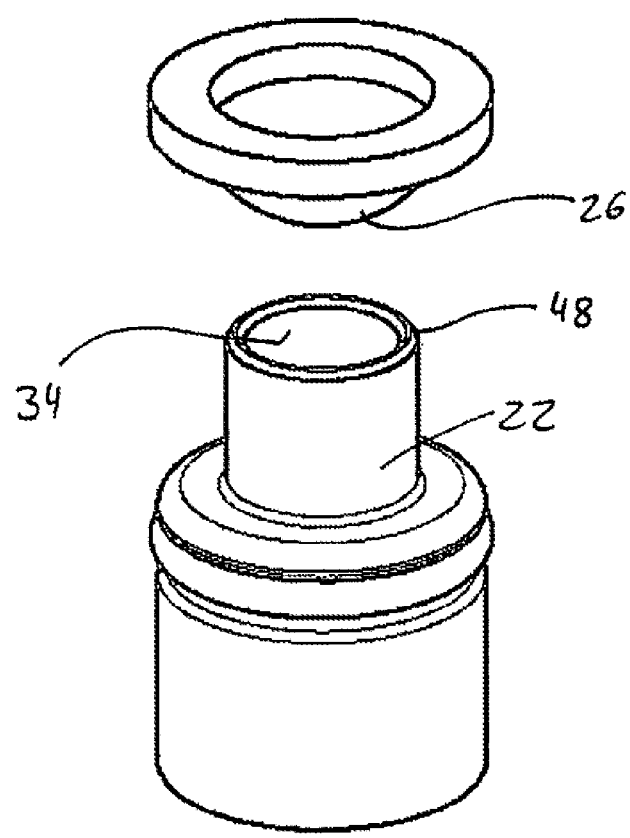
FIG. 10 shows the dome valve from FIG. 9 from a further angle of view.

FIG. 10 shows the components shown in FIG. 9 from a different angle of view. The advantage of said development compared to the representation of a pin 22 shown in FIG. 8 is that the pin 22 in the exemplary embodiment shown in FIGS. 9 and 10 does not have to push through the longitudinal slot 46 of the diaphragm 26 and consequently cannot damage it when pushing through and when being pulled out. A valve 24, which includes a pin 22 according to FIGS. 9 and 10, is consequently less susceptible to faults and has a longer service life.

Figure 11:
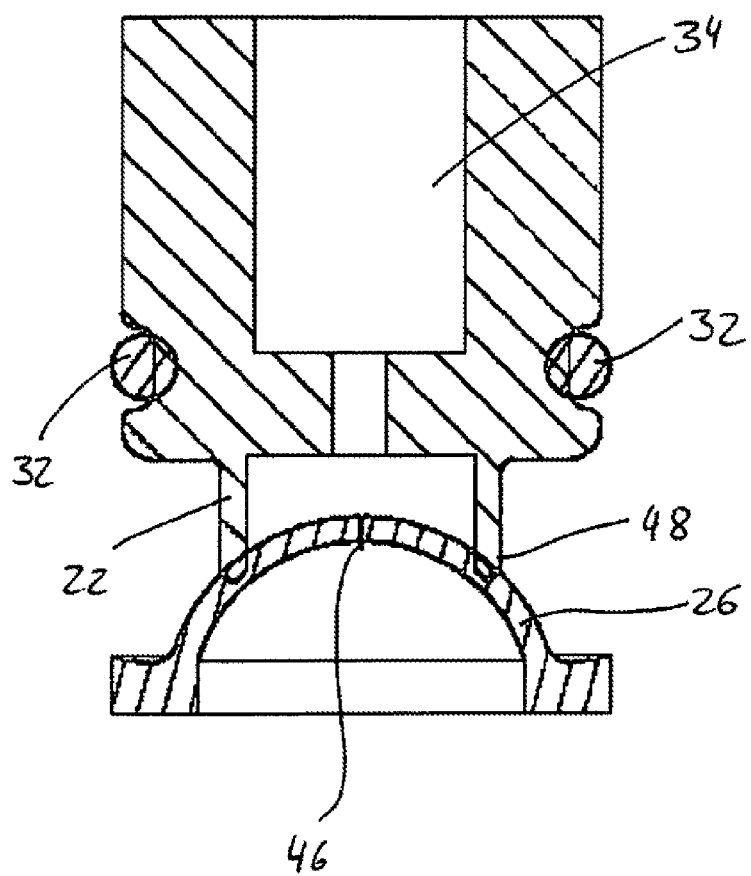
FIG. 11 shows a schematic sectional representation of the dome valve from FIGS. 9 and 10.

FIG. 11 shows the situation where the pin 22 according to FIGS. 9 and 10 abuts against the diaphragm 26 of the valve 24. As a result, the longitudinal slot 46 is opened and the valve 24 can be used as a two-way valve.

Figure 12:
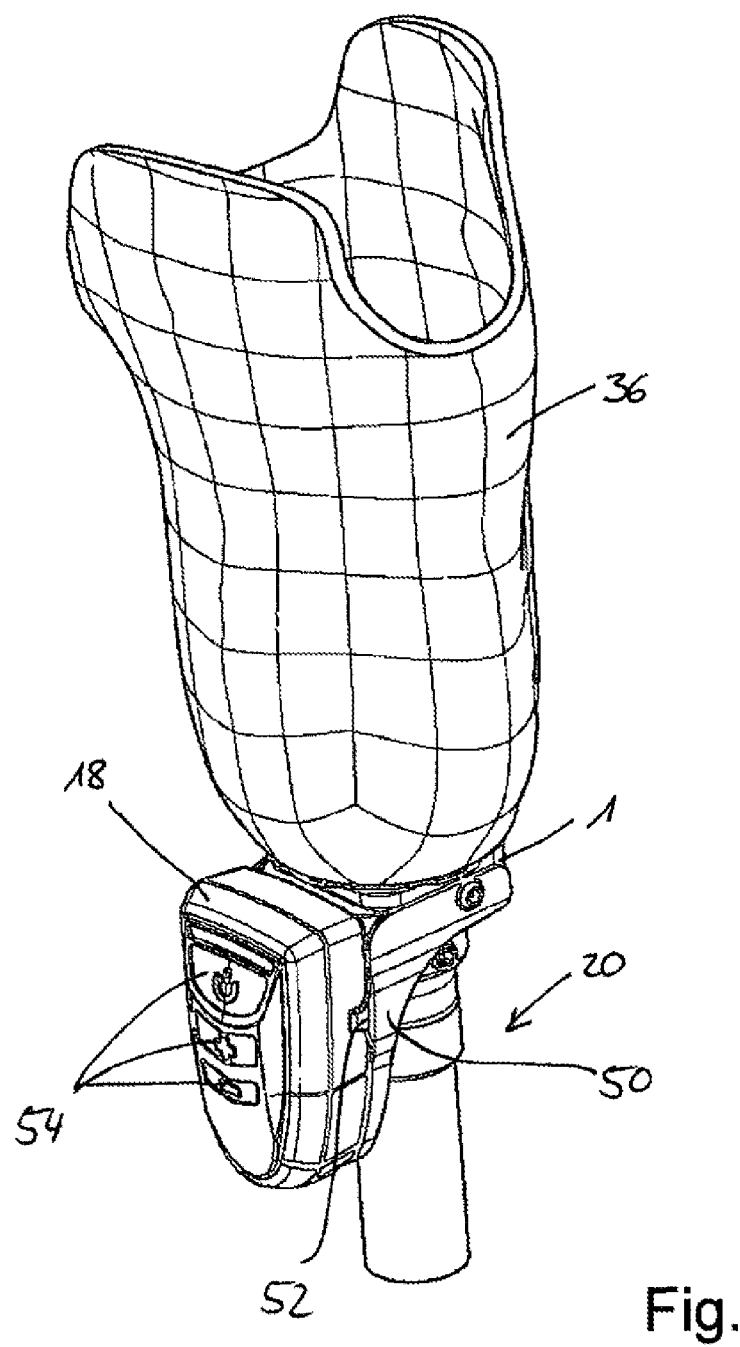
FIG. 12 shows a schematic representation of a prosthesis system according to an exemplary embodiment of the present invention.

FIG. 12 shows the schematic representation of a prosthesis system according to an exemplary embodiment of the present invention. The prosthesis shaft 36 is shown in the top part whilst the prosthesis structure 20 extends at the bottom end of the prosthesis system. The adapter element 1, which in the present exemplary embodiment is almost completely covered by a connecting plate 50 which is fastened to it, is situated in between. The connecting plate 50 has latch-type or snap-type elements 52 by means of which the pump housing 18 is connectable to the connecting plate 50. Various control elements 50, by means of which the operation of the pump is able to be influenced, are provided on the outside surface of the pump housing 18.

The provision of the separate connecting plate 50 with the latch-type or snap-type elements 52 located thereon provides a particularly simple and nevertheless secure and space-saving possibility for fastening the pump housing 18.

Figure 13:
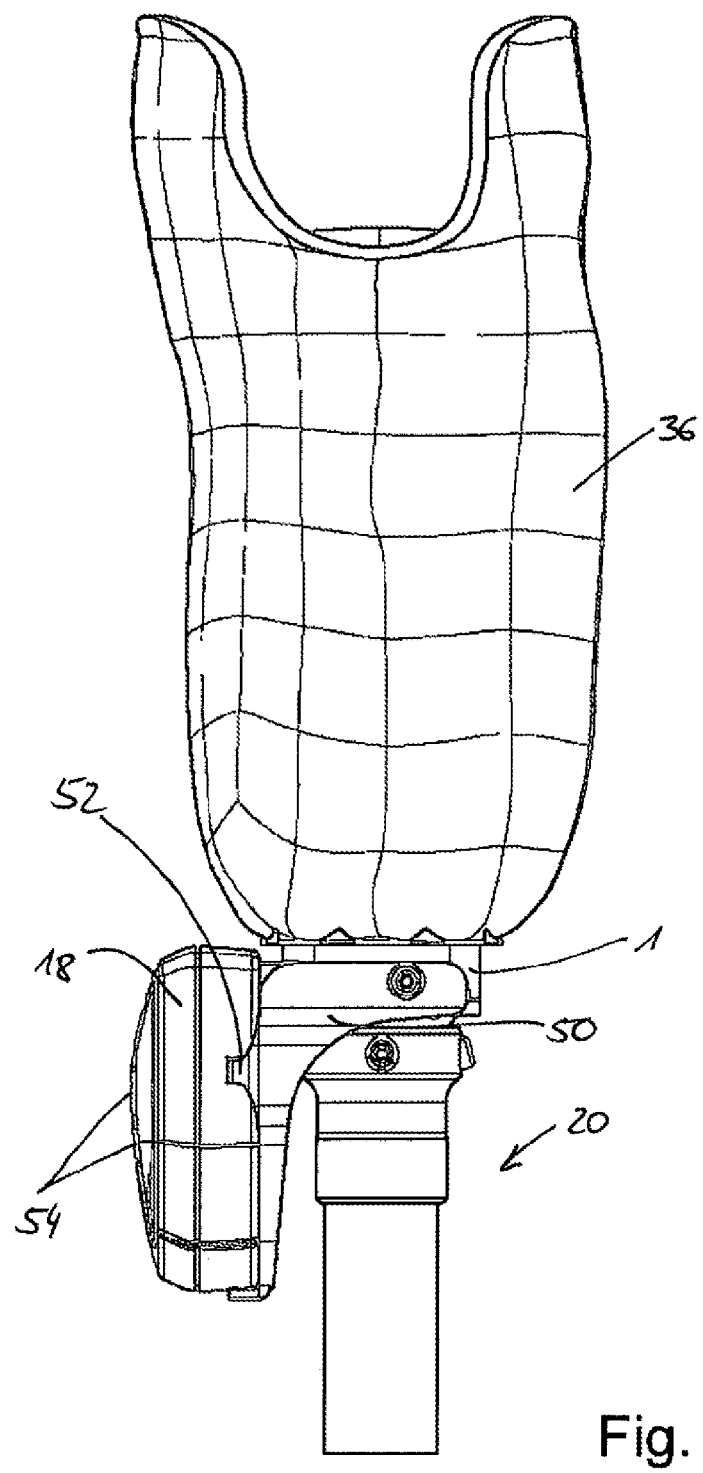
FIG. 13 shows a side view of the representation from FIG. 11.

FIG. 13 shows a side view of the prosthesis system from FIG. 12. The special development of the connecting plate 50 makes it possible to fasten the pump housing 18 in as space-saving and unobtrusive a manner as possible and nevertheless to ensure it is extremely easy to reach by the wearer of the prosthesis system.

Figure 14:
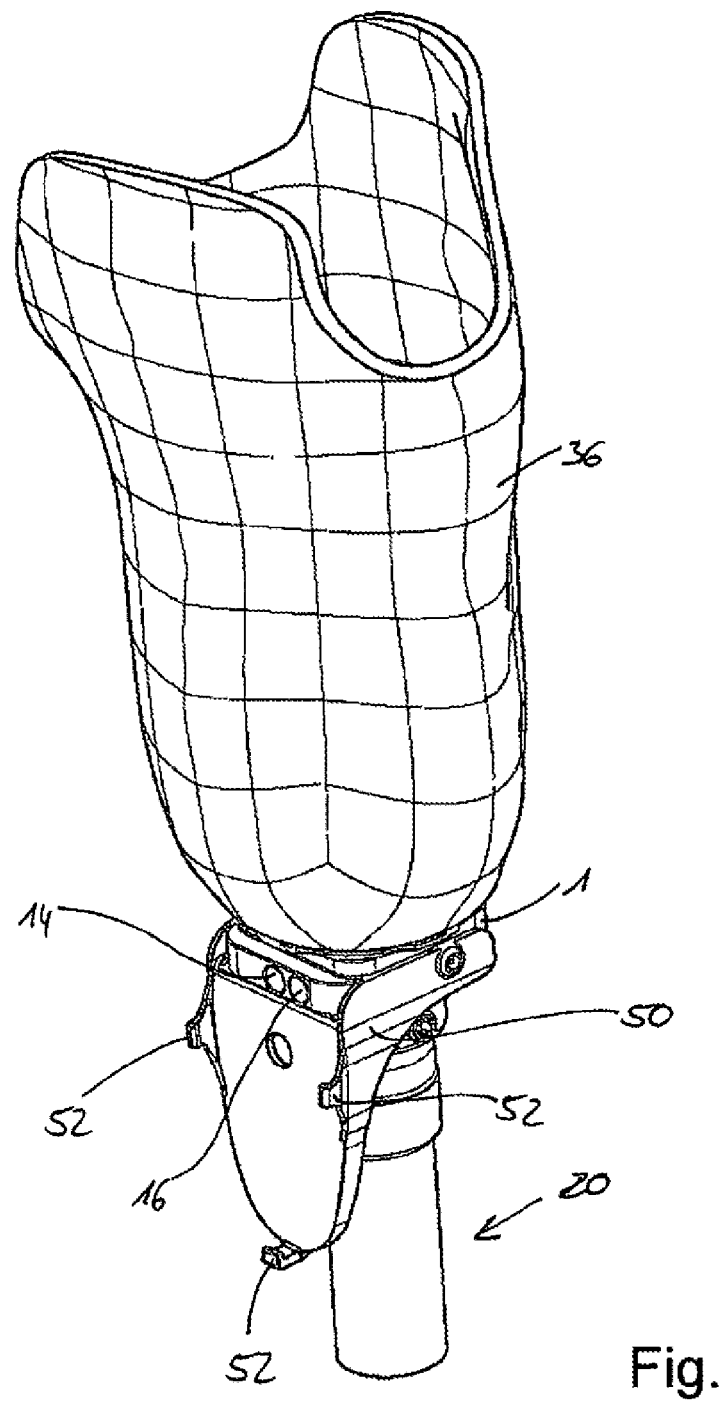
FIG. 14 shows the schematic view of a prosthesis system according to a further exemplary embodiment of the present invention.

FIG. 14 shows the prosthesis system from FIGS. 12 and 13 where the pump housing 18 has been removed. On the side on which the pump housing 18 is to be connected to the connecting plate 50, the connecting plate 50, in the exemplary embodiment shown, has three latch-type or snap-type elements 52 by means of which a secure and vibration-proof bearing arrangement of the pump housing 18 on the connecting plate 50 is ensured. In addition, the adapter element 1 also has a force-applying element 16 which, as already described, can be developed, for example, in the form of a magnet.

The second orifice 14 of the adapter element 1 to which the pump (not shown) is connected, is shown next to said force-applying element.

Figure 15:
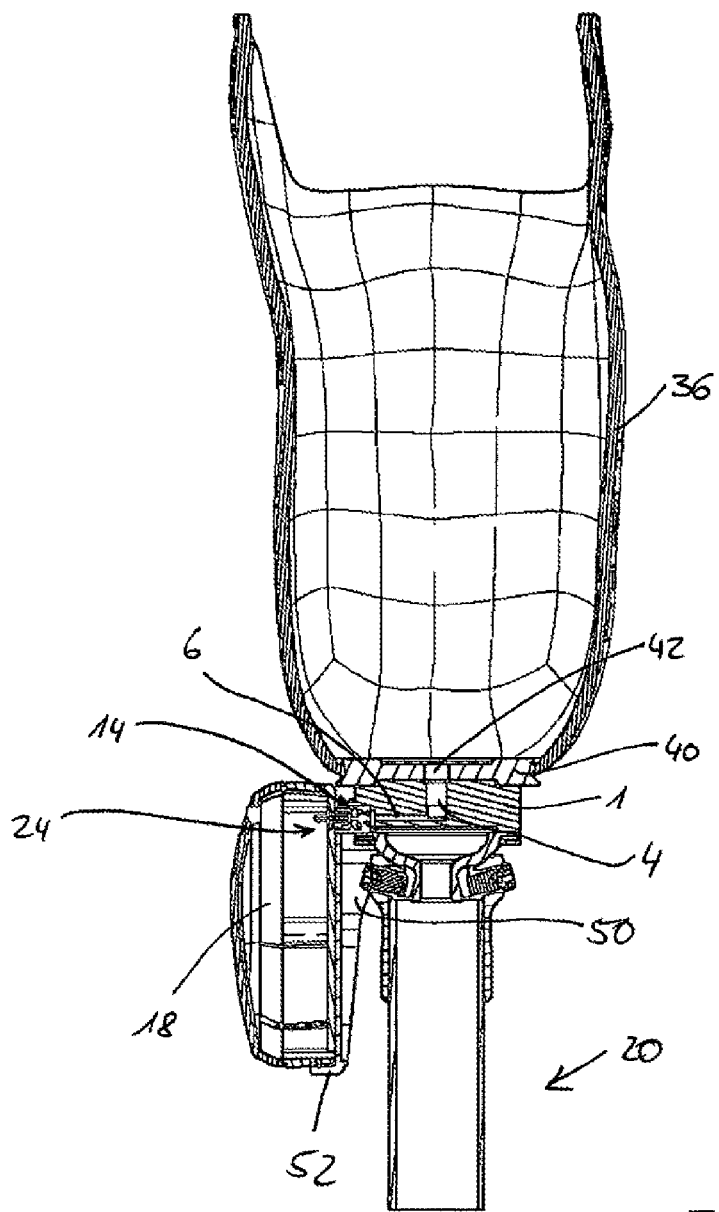
FIG. 15 shows a sectional representation of the representation from FIGS. 11 and 12 and FIG. 16 shows an enlarged detail from FIG. 14.

FIG. 15 shows a sectional representation of the representation from FIGS. 12 and 13. The through-bore 42, which is connected by means of the first orifice 4 to the channel 6 of the adapter element 1, is situated at the bottom end of the prosthesis shaft 36. The valve 24 is shown at the second orifice 14 of the channel 6. The central region of FIG. 15 is shown in an enlarged manner in FIG. 16.

The valve 24 has the diaphragm 26, which has, for example, a longitudinal slot 46, as is shown for example in FIGS. 8 and 9. The pin 22 with the passage 34 located therein pushes through said longitudinal slot. As a result, the valve 24, in the situation shown in FIG. 16, is operated in the form of a two-way valve such that the inner volume 44 which is situated between the prosthesis shaft 36 and the liner 38 (not shown in FIG. 16) is able to be evacuated by the pump which is situated in the pump housing 18.

Figure 16:
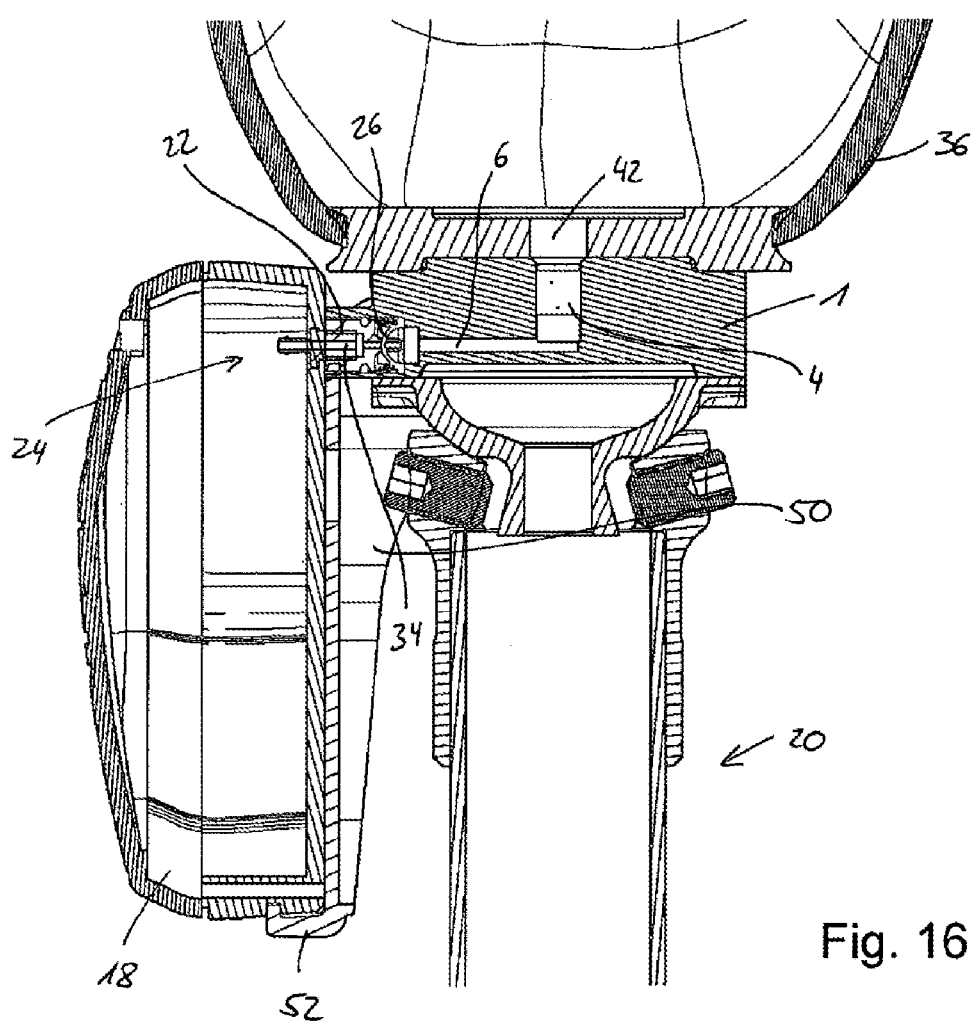

Once a sufficiently strong negative pressure has been produced in this manner, it is possible either to remove the pump itself with the pump housing 18 from the connecting plate 50, as a result of which the pin 22, in the embodiment shown in FIG. 16, is snapped back to the left. As a result, the pin 22 no longer penetrates the diaphragm 26 and the valve 24 is still only operated in the form of a one-way valve.

Figure 17:
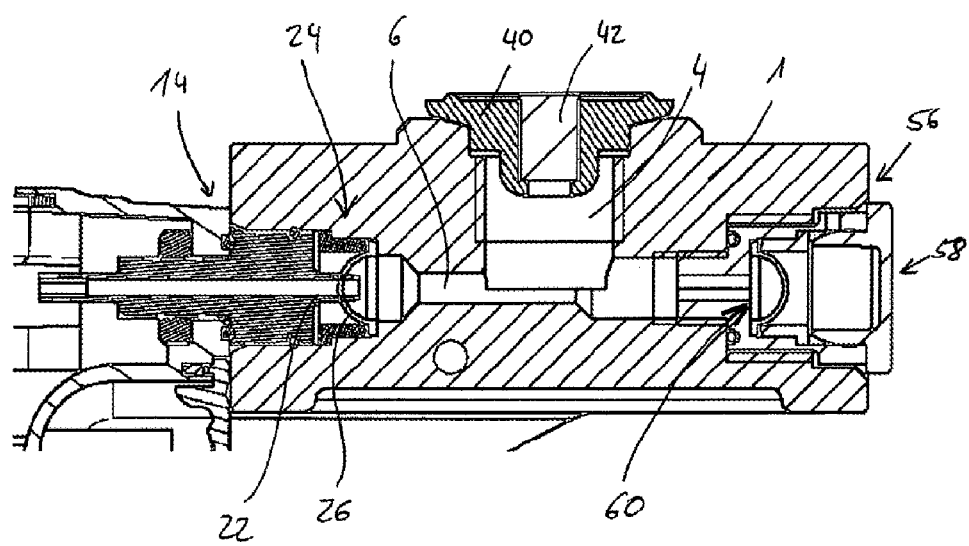
FIG. 17 shows a schematic representation of a detail from a prosthesis system according to a further exemplary embodiment of the invention.

FIG. 17 shows the adapter element 1 with the channel 6, the first orifice 4 and the second orifice 14 in which the valve 24 is situated with the diaphragm 26 which is pushed through by the pin 22 of the pump. A sealing element 82 which enables an air-tight connection to the fastening device 40 of a prosthesis shaft (not shown) is arranged in the first orifice 4. The through-bore 42 is situated in said prosthesis shaft. The adapter element 1 shown in FIG. 17 also has a third orifice 56 in which a closure element 58 is situated. Said closure element has a one-way valve 60 which allows air to emerge only to the right in the exemplary embodiment shown in FIG. 17. The closure element 58 is shown in more detail in FIG. 18. It is possible to see a valve diaphragm 62 which allows the passage of air from left to right in the representation shown, but prevents it, however, from right to left. The valve diaphragm 62 fits between a valve holder 64 and a valve housing 66. A sealing ring 68, which prevents air passing through between the wall of the third orifice 56 and the valve housing 66, is situated in the valve housing 66.

A protective cap 70, which protects the valve from contamination, is shown in the right-hand region of the closure element. An outlet bore 72, through which gas which has passed through the valve is able to leave the closure element 58 past the protective cap 70, is situated in the top region of the valve housing 66.

Figure 18:
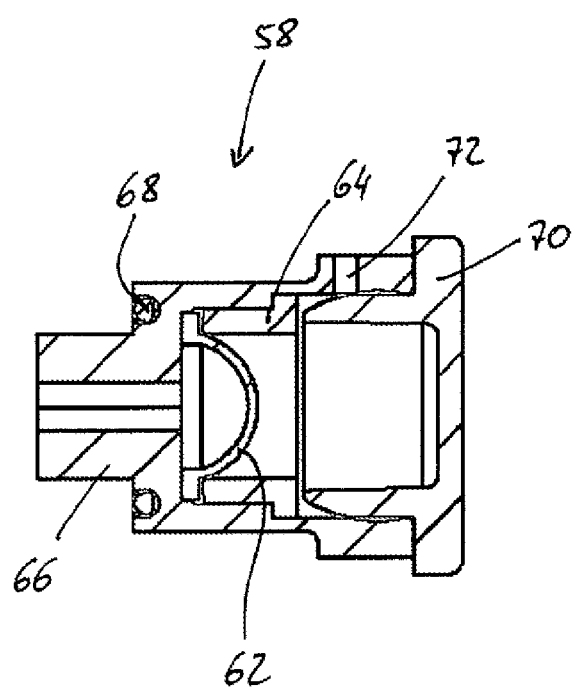
FIG. 18 shows a sectional representation of a closure element for a device according to a further exemplary embodiment of the present invention.
Figure 19:
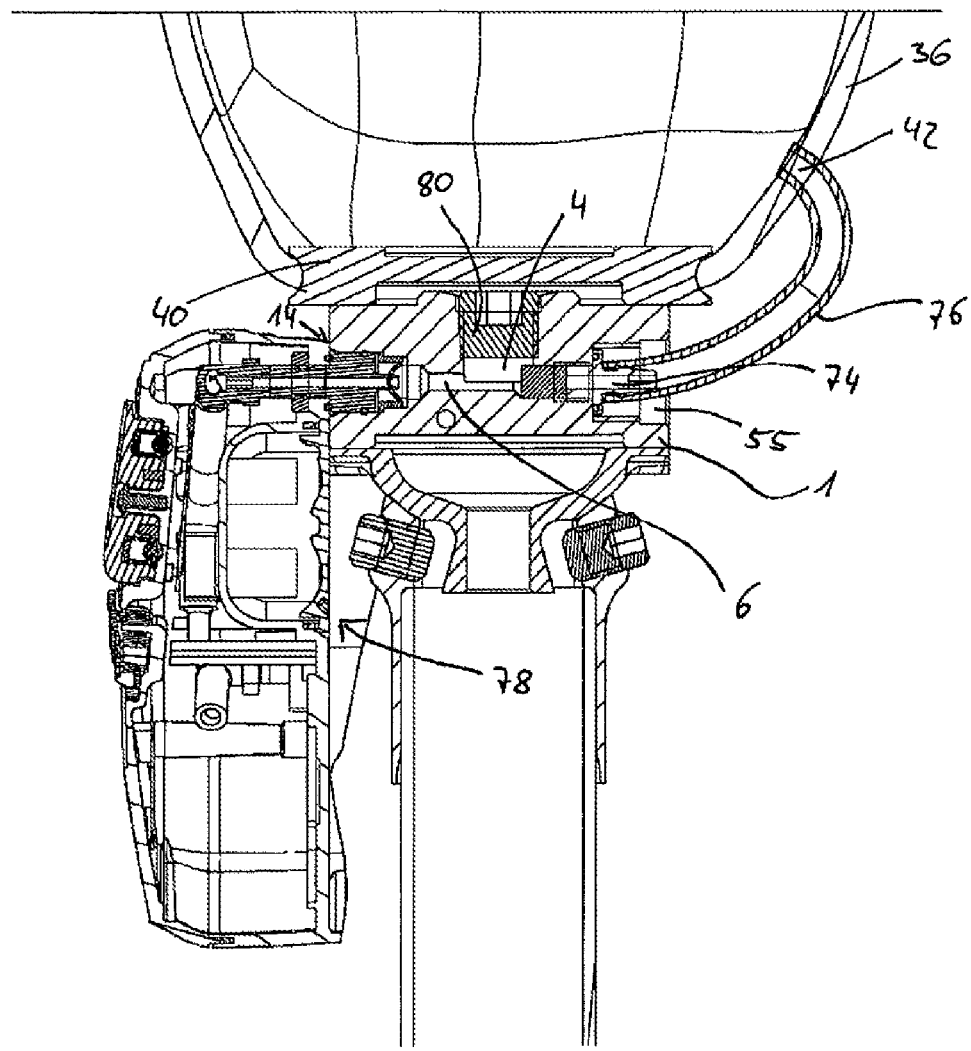
FIG. 19 shows a schematic sectional representation through a detail of a prosthesis system according to a further exemplary embodiment of the present invention.

FIG. 19 shows a schematic sectional representation through a detail of a prosthesis system. It is possible to see the adapter element which has the first channel 6 which, in the exemplary embodiment shown, comprises the third orifice 56. The closure element 58, however, is not situated in said third orifice, as is shown in FIG. 18, but rather a hose connection 74 on which a hose 76 is arranged. Said hose is connected to the through-bore 42 in the prosthesis shaft 36. Air is therefore pumped out of the prosthesis shaft 36 through the hose connection 74 and the hose 76 by means of an arranged pump 78 which is connected to the second orifice 14. The first orifice 4 of the channel 6 is closed by means of a closure element 80. The embodiment shown is of interest in the case where the fastening device 40 of the prosthesis shaft 36 does not comprise a through-bore on the side that faces the first orifice 4.

Figure 20:
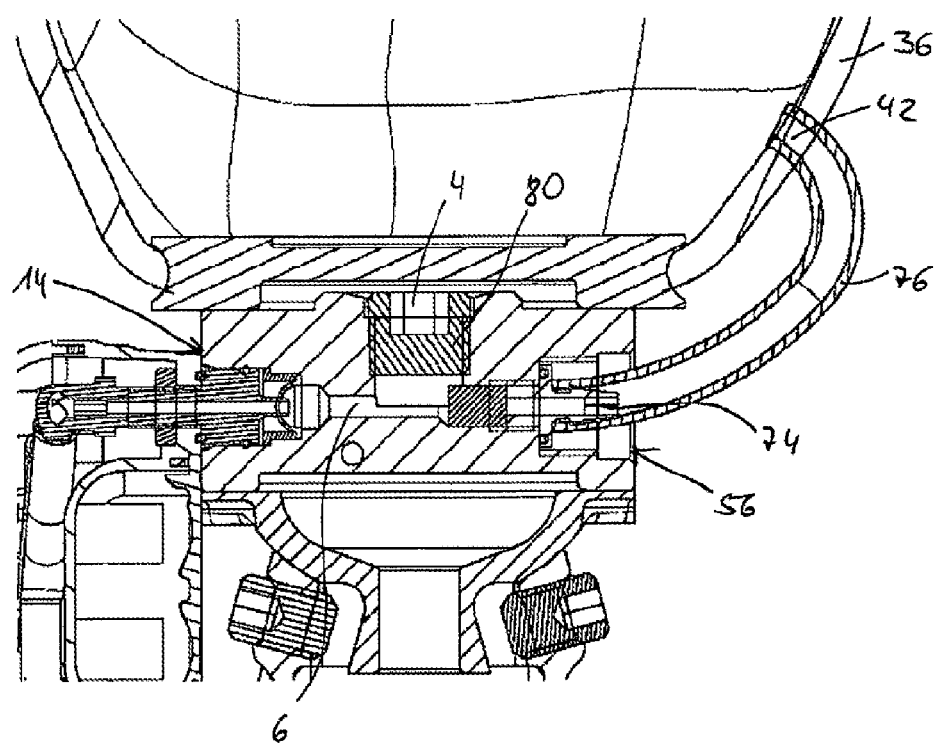
FIG. 20 shows an enlarged detail from FIG. 19.

FIG. 20 shows an enlarged detail from FIG. 19.

Figure 21:
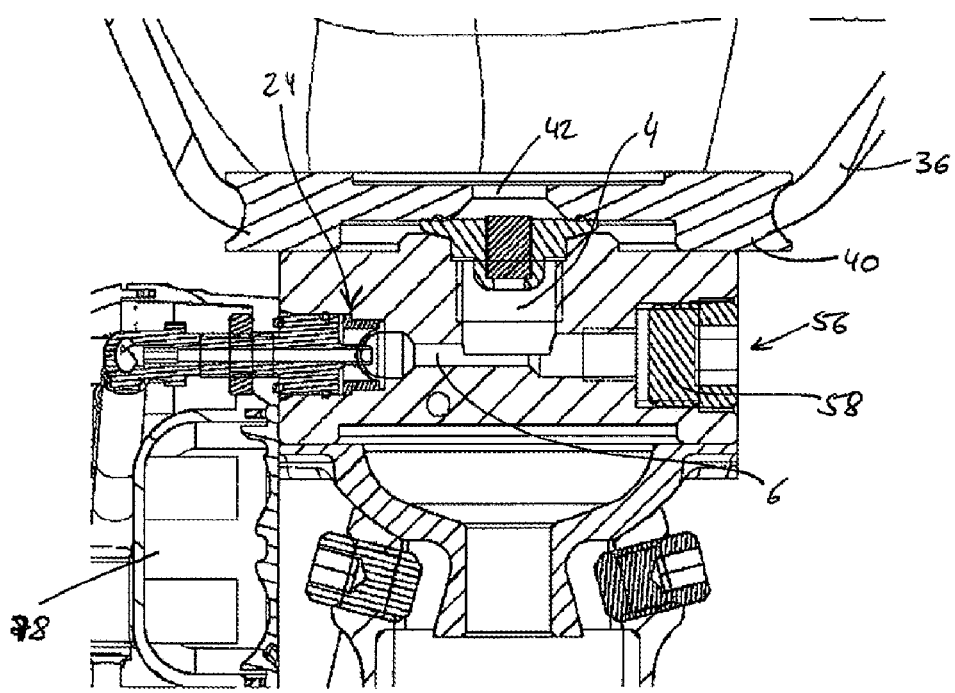
FIG. 21 shows the detail from FIG. 20 with another closure element in the device and FIG. 22 shows the detail from FIGS. 20 and 21 with a further closure element.

FIG. 21 shows the same detail, the fastening device 40 of the prosthesis shaft 36, however, now comprising the through bore 42 on the side that faces the first orifice 4 and being connected to the adapter element 1 by means of the sealing element 82. The pump 78 consequently pumps air out of the channel 6 through the valve 24, said air passing through the first orifice 4 and the through-bore 42 out of the interior region of the prosthesis shaft 36 into the channel 6. The third orifice 56 is closed by way of the closure element 58 in the exemplary embodiment shown. In this case, the closure element 58 shown here forms simply one closure so that air is neither able to penetrate into the channel 6 nor to pass out of it through the third orifice 56. In this way, the function achieved is the same as is shown in the exemplary embodiment shown in FIG. 15 where the adapter element 1 or the at least one channel 6 only comprises a first orifice 4 and a second orifice 14.

Figure 22:
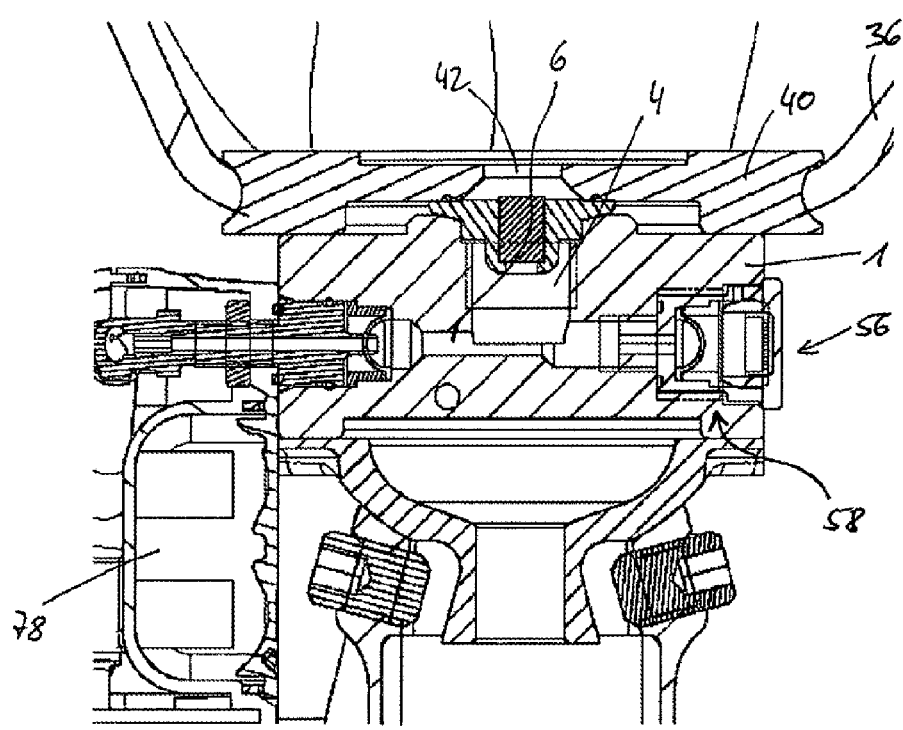

FIG. 22 once again shows a corresponding detail where the adapter element 1 is connected to the fastening device 40 of the prosthesis shaft 36 by means of the sealing element 82. The through-bore 42 is situated in the fastening device 40 again and consequently on the side that faces the first orifice 4 of the channel 6. The pump 78 therefore, as in the exemplary embodiment shown in FIG. 21, pumps air out of the inner region of the prosthesis shaft 21. The closure element 58, which has already been shown is FIG. 18, is now situated in the third orifice 56. Air out of the channel 6 can consequently leave the channel 6 through the closure element 58 and the third orifice 56. This is particularly advantageous if, for example as a result of a small leak, gas collects in the prosthesis shaft 36 of the prosthesis system. Said gas is pressed through the through-bore 42 into the channel 6 as a result of a walking movement of the patient. Insofar as the pump 78 is not operating, the gas cannot leave the channel through the second orifice 14. Instead of which it is possible to remove the gas out of the channel 6 and the vacuum, which is desired inside the prosthesis shaft in order to fix the prosthesis to the amputation stump of the patient, can consequently be maintained without the pump 78 having to be switched on. As a result, energy can be saved, the noise load reduced and in addition the service life of the pump increased.

Figure 23:
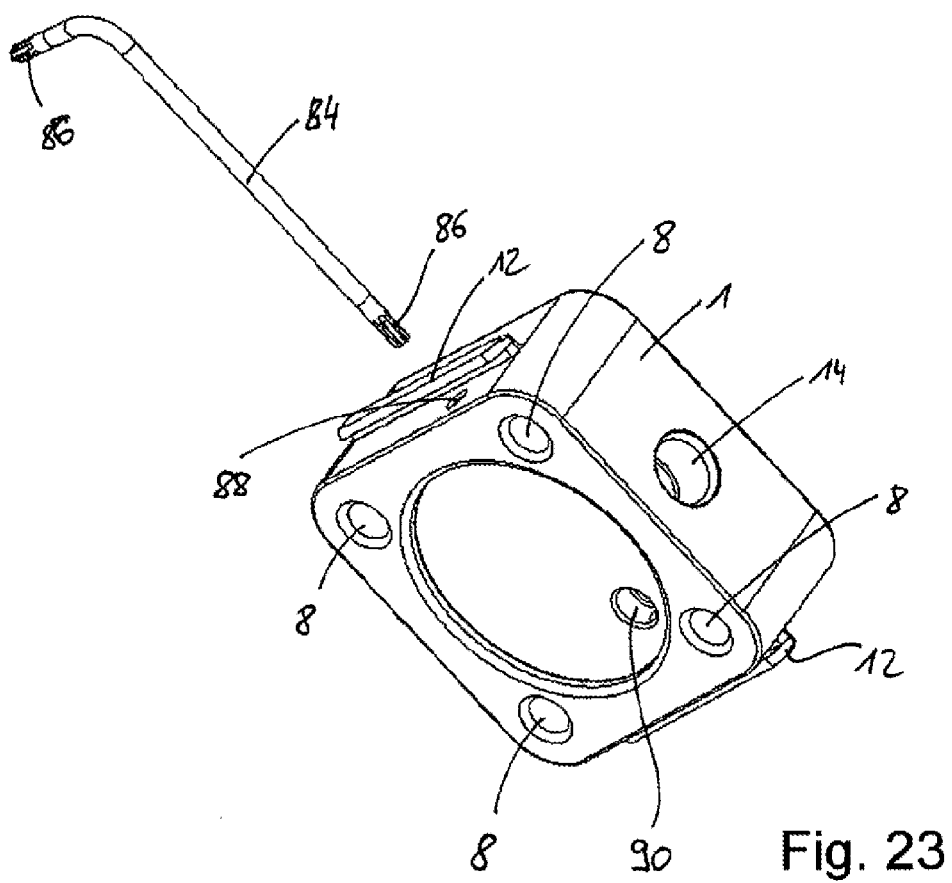
FIG. 23 shows the schematic representation of a device according to a further exemplary embodiment of the present invention.

FIG. 23 shows the adapter element 1 according to a further exemplary embodiment of the present invention. It has four bores 8 as well as connecting means 12 which are realized in the exemplary embodiment shown in FIG. 23 in the form of hook-shaped projections which extend over almost the entire side length of the adapter element 1. The second orifice 14 can be seen on a side face.

A plug-in element 84, which has a socket wrench 86 at each of its two ends, is shown along with the adapter element 1. The plug-in element 84 can be pushed into an insert bore 88 which is provided in the adapter element 1 for that purpose.

A further insert bore 88, which is arranged such that the two insert bores 88 on the adapter element 1 and on the pump housing 18 are in alignment with one another, is situated in the pump housing 18 which is not shown in FIG. 23. In said state, the plug-in element 84 is inserted into the insert bores 88 and thus ensures that the two parts are locked and fastened to one another.

A ball pin bore 90, in which a ball pin (not shown in FIG. 23) is guided in a spring-loaded manner, can also be seen on the adapter element 1 in FIG. 23. If the plug-in element 84 is inserted into the insert bore 88, this causes the ball pin to be displaced in opposition to the spring that loads it such that the achievement here is that the connection is further fastened and reinforced.

Figure 24:
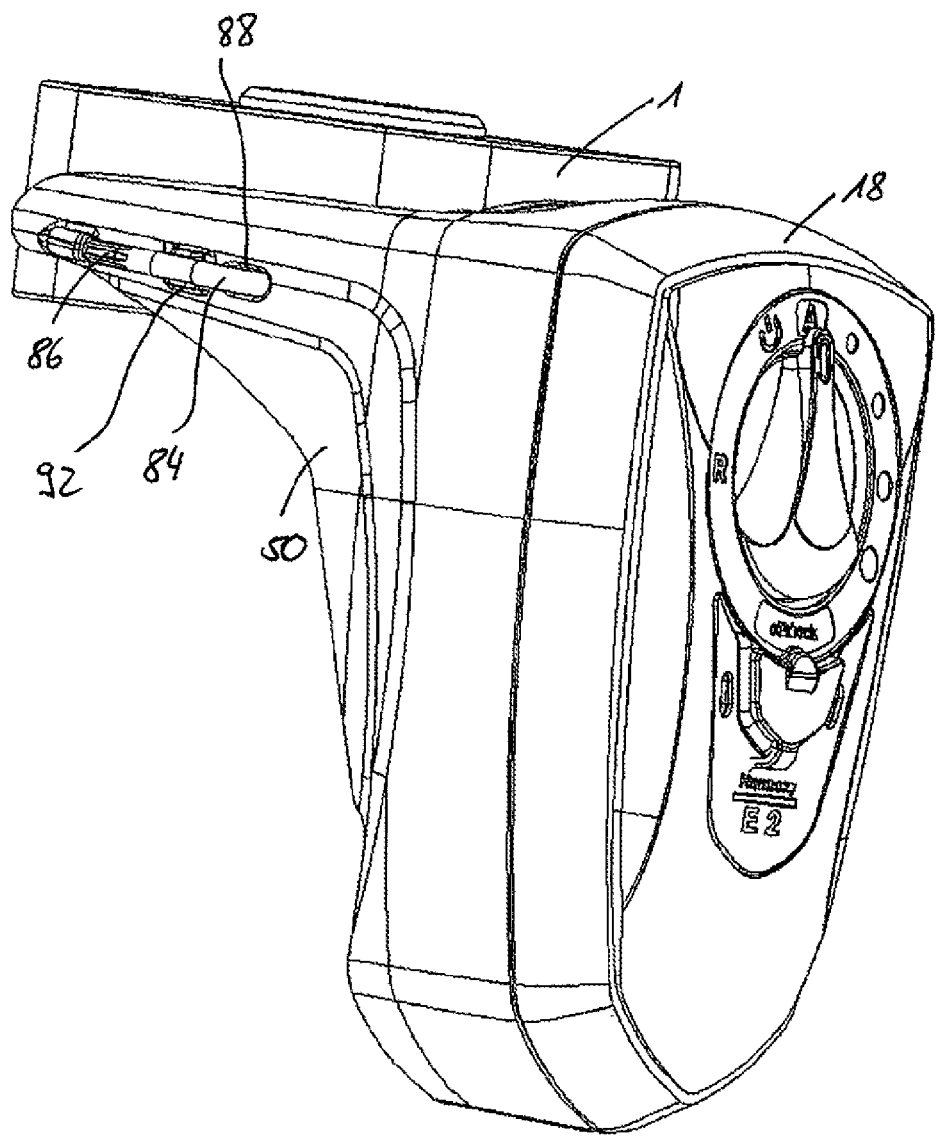
FIG. 24 shows the schematic representation of the device from FIG. 23 with a pump housing and FIG. 25 shows a schematic sectional representation through a detail from FIG. 24.

FIG. 24 shows the adapter element 1 which is connected to the pump housing 18 by means of the connecting plate 50 which has already been shown in FIG. 13. It is possible to see part of the plug-in element 84 which is inserted into the insert bore 88 of the pump housing 18 as well as the insert bore 88 of the adapter element 1 (cannot be seen in FIG. 24). The protruding part of the plug-in element 84 is arranged in a clip element 92 and is thus secured against slipping out of the insert bores 88. The socket wrench 86 is shown at the end of the plug-in element.

Figure 25:
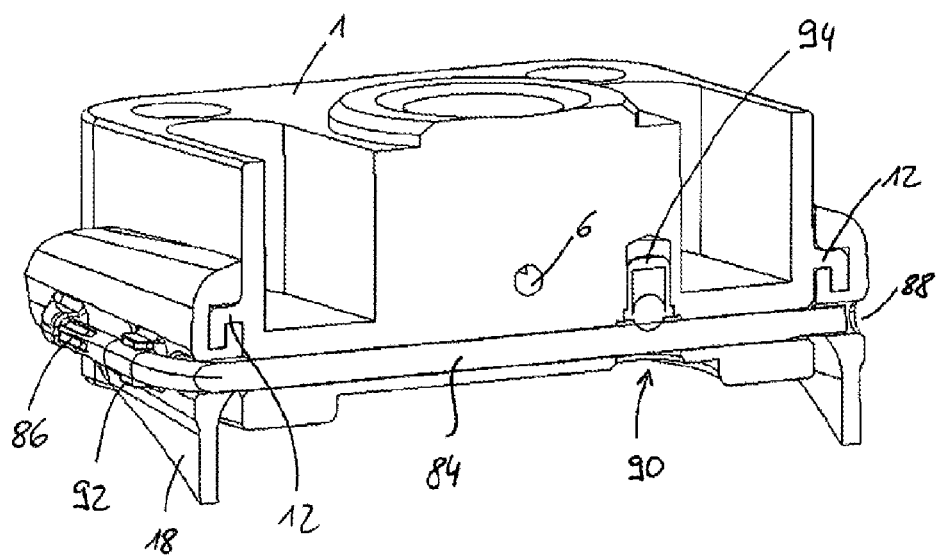

FIG. 25 shows a sectional representation of the adapter element 1 as well as of part of the pump housing 18. The connecting means 12, which comprise a hook-shaped cross section and have been inserted into a correspondingly formed groove on the pump housing 18, can be seen on the side of the adapter element 1. The section of the sectional representation of FIG. 25 extends precisely through the insert bore 88 in which the plug-in element 84 is shown in FIG. 25. The protruding end is arranged in the clip element 92 again and is secured against slipping out.

A ball pin 94, which is spring-loaded downward by means of a spring (not shown) in FIG. 25, is now shown inside the ball pin bores 90. By means of the inserted plug-in element 84 the ball pin 94 is pressed upward against the spring that loads it and, as a result, then exerts a force onto the plug-in element 84 which ensures a secure hold. In order to reinforce said effect, a reduction in the cross section of the plug-in element 84 can be provided in the region in which, with the plug-in element 84 inserted, the ball pin 94 is located, such that a further latch-type connection is produced here. The channel 6 can be seen in the sectional face of the adapter element 1.

| List of references | |
|---|---|
| 1 | Adapter element |
| 2 | Top side |
| 4 | First orifice |
| 6 | Channel |
| 8 | Bore |

| List of references (continued) | |
|---|---|
| 10 | Groove |
| 12 | Connecting means |
| 14 | Second orifice |
| 16 | Force-applying element |
| 18 | Pump housing |
| 20 | Prosthesis structure |
| 22 | Pin |
| 24 | Valve |
| 26 | Diaphragm |
| 28 | Tongue element |
| 30 | Sealing ring |
| 32 | Sealing ring |
| 34 | Passage |
| 36 | Prosthesis shaft |
| 38 | Liner |
| 40 | Fastening device |
| 42 | Through-bore |
| 44 | Inner volume |
| 46 | Longitudinal slot |
| 48 | Pressure edge |
| 50 | Connecting plate |
| 52 | Latch-type or snap-type element |
| 54 | Control element |
| 56 | Third orifice |
| 58 | Closure element |
| 60 | One-way valve |
| 62 | Valve diaphragm |
| 64 | Valve holder |
| 66 | Valve housing |
| 68 | Sealing ring |
| 70 | Protective cap |
| 72 | Outlet bore |
| 74 | Hose connection |
| 76 | Hose |
| 78 | Pump |
| 80 | Closure element |
| 82 | Sealing element |
| 84 | Plug-in element |
| 86 | Socket wrench |
| 88 | Insert bore |
| 90 | Ball pin bore |
| 92 | Clip element |
| 94 | Ball pin |

The invention claimed is:

1. A device for connecting a pump to a through-bore which is provided in a prosthesis socket, the device comprises:
at least one channel comprising:
a first orifice for connecting to the through-bore provided in the prosthesis socket;
a second orifice which is connectable to the pump;
at least one valve, the at least one valve being movable into a first mode in which the at least one valve operates as a one-way valve and into a second mode in which the at least one valve operates as a two-way valve, wherein when the at least one valve is in the first mode, air flows through the at least one valve and the at least one channel only in a first direction from the first orifice to the second orifice, and when the at least one valve is in the second mode, air flows through the at least one valve and the at least one channel in the first direction and in a second direction from the second orifice to the first orifice;
wherein the at least one valve includes a diaphragm and an outwardly projecting pin configured to push through the diaphragm or open the diaphragm as a result of pressure applied to the diaphragm when the pump housing is connected to the device, the outwardly projecting pin being arranged on the pump housing.

2. The device as claimed in claim 1, wherein the valve is movable from the first mode into the second mode by the diaphragm being pushed through by a push-through element or by being opened by pressure applied to the diaphragm.

3. The device as claimed in claim 1, wherein the at least one channel comprises a third orifice for connecting to the through-bore provided in the prosthesis socket and an end element which is connectable to the third orifice and in a connected state prevents inflow through the third orifice into the at least one channel.

4. The device as claimed in claim 3, wherein the end element comprises a one-way valve which, with the end element connected to the third orifice, only allows outflow through the third orifice out of the at least one channel.

5. A system having a device as claimed in claim 1, a pump with a pump housing, and connecting members, wherein the connecting members correspond with one another and operate to connect the device to the pump housing, the connecting members being positioned on the pump housing and on the device.

6. The system as claimed in claim 5, wherein the connecting members include at least one groove and one tongue which corresponds to the groove.

7. The system as claimed in claim 5, wherein the connecting members include a connecting plate which is provided on the device.

8. The system as claimed in claim 5, further comprising a first force-applying element arranged on the pump housing and a second force-applying element arranged on the device, the first and second force-applying elements together producing a force when the pump housing is connected to the device, wherein the force counters a releasing of the pump housing from the device.

9. The system as claimed in claim 8, wherein a first insert bore is provided on the pump housing and a second insert bore is provided on the device, the first and second insert bores being aligned with one another in a connected state such that a plug-in element is guidable through the first and second insert bores.

10. A prosthesis system having a prosthesis socket and a system as claimed in claim 5.

11. A prosthesis system having a prosthesis socket and a device as claimed in claim 1.

12. A device, comprising:
a prosthetic socket having a through-bore;
a pump connected to the through-bore of the prosthesis socket;
at least one channel, comprising:
a first orifice connected to the through-bore;
a second orifice connected to the pump;
at least one valve that is movable between a first mode in which the at least one valve is operable as a one-way valve and a second mode in which the at least one valve is operable as a two-way valve, the first mode permitting air flow through the at least one valve and the at least one channel in only a first direction from the first orifice to the second orifice, and the second mode permitting air flow through the at least one valve and the at least one channel in the first direction and in a second direction from the second orifice to the second orifice;
wherein the at least one valve includes a diaphragm and an outwardly projecting pin configured to push through the diaphragm or open the diaphragm as a result of pressure applied to the diaphragm when the pump housing is connected to the device, the outwardly projecting pin being arranged on the pump housing.

13. The device as claimed in claim 12, wherein the at least one valve is movable from the first mode to the second mode when the diaphragm is pushed through by a push-through element or is opened by pressure applied to the diaphragm.

14. The device as claimed in claim 12, wherein the at least one channel comprises a third orifice, the third orifice being connected to the through-bore, and an end element which is connectable to the third orifice, the end element being operable to limit inflow through the third orifice into the at least one channel when connected to the third orifice.

15. The device as claimed in claim 14, wherein the end element comprises a one-way valve which only allows outflow through the third orifice out of the at least one channel when the end element is connected to the third orifice.

16. A system comprising the device as claimed in claim 12, and mating first and second connecting members, wherein the pump includes a pump housing, and the first connecting member is mounted to the device and the second connecting member is mounted to the pump housing.

17. The system as claimed in claim 16, wherein one of the first and second connecting members comprises a groove and the other of the first and second connecting member comprises a tongue which mates with the groove.

* * * * *